United States Patent [19]

Overmyer

[11] Patent Number: 5,076,787
[45] Date of Patent: Dec. 31, 1991

[54] VARIABLE SUCTION ASPIRATOR HEAD WITH SOLIDS TRAP

[76] Inventor: Thad J. Overmyer, 132 N. Second St., Danville, Ky. 40422

[21] Appl. No.: 746,490

[22] Filed: Aug. 16, 1991

[51] Int. Cl.⁵ .............................................. A61C 17/06
[52] U.S. Cl. ........................................ 433/95; 433/92; 604/119; 604/902
[58] Field of Search ...................... 433/92, 95; 604/33, 604/119, 902

[56] References Cited

U.S. PATENT DOCUMENTS

| | | | |
|---|---|---|---|
| 2,180,063 | 11/1939 | McKinley | 604/33 |
| 2,885,782 | 5/1959 | Groves | 433/95 |
| 3,476,144 | 11/1969 | Krantz | 433/95 |
| 3,678,959 | 7/1972 | Liposky | 604/33 |
| 3,834,388 | 9/1974 | Sauer | 604/119 |
| 4,031,896 | 6/1977 | Ronnmark | 604/119 |
| 4,430,073 | 2/1984 | Bemis et al. | 604/119 |
| 4,487,600 | 12/1984 | Brownlie et al. | 604/119 |
| 4,880,411 | 11/1989 | Fangrow, Jr. et al. | 604/119 |

*Primary Examiner*—John J. Wilson
*Attorney, Agent, or Firm*—Charles J. Brown

[57] ABSTRACT

A variable suction aspirator head for an end fitting of a suction hose consisting simply of an inner valve tube having wall holes and a slideable outer barrel, permitting variations in suction, the trapping of solid material by the valve tube wall holes and easy disassembly for cleaning and sterilization of the parts after each use.

8 Claims, 3 Drawing Sheets

VARIABLE SUCTION ASPIRATOR HEAD WITH SOLIDS TRAP

BACKGROUND OF THE INVENTION

Dental and medical instruments used on successive patients in contact with saliva or other body fluids or solids must be capable of total cleaning and sterilization after each use to prevent transmission of communicable disease. Variable suction devices such as those used by dentists to remove saliva and dental debris from the mouth are particularly in need of improvement in this regard.

Typical dental aspirator heads have a rotary valve for varying suction, as for example that shown in U.S. Pat. No. 2,885,782. However these are complicated devices with many movable parts and cannot as a practical matter be disassembled after each use for cleaning and sterilization. Many cannot even be detached from their associated suction hoses.

Moreover prior art dental aspirator heads are designed to draw all material from the mouth, not only saliva but solid debris as well and the solid material is allowed to collect in a trap of the waste disposal system of the dental facility and is only periodically removed such as once each day. During the hours while solid dental debris remains in the trap it could well be the source of contamination migrating downstream into sewage systems.

Some slide valve variable suction heads are known, such as that described in U.S. Pat. No. 3,834,388 but they are incapable of trapping solids and many are almost as complicated as rotary valve forms, as for example the slide valve design disclosed in U.S. Pat. No. 4,487,600.

Disposable traps for solids in aspiration systems are of course known as such, that described in U.S. Pat. No. 4,880,411 being one example, but not in variable suction head devices and particularly in hand-held aspirator heads used in dental procedures.

The principal object of the present invention is to provide a variable suction aspirator head which is of an irreducible minimum of parts, which can easily be assembled and disassembled for complete cleaning and sterilization of those parts after each successive use, and which is capable of trapping solids in the head itself so that they are not carried downstream to pose a contamination threat.

SUMMARY OF THE INVENTION

The invention provides a variable suction aspirator head with a solid trap for aspiration of material as from the mouth of a dental patient, the head having a rearward suction source end attached to an end fitting of a suction hose and a forward aspirating end. The head comprises a valve tube and a barrel. The valve tube extends forwardly from and is fixed to the end fitting and it comprises a shaft adjacent the end fitting, a foraminous portion forwardly of and of the same outside diameter as the shaft and formed with longitudinally spaced wall holes, and a cap closing off the forward end of the foraminous portion. The barrel comprises an end annulus sized to sealingly and slidably encircle the tube shaft and adapted to be reciprocated along the foraminous portion to cover and uncover various of said holes. An enlarged portion is also included in the barrel forwardly of the end annulus and is adapted to define a chamber around the tube foraminous portion. The barrel also includes a tubular wand forwardly of the enlarged portion of aspirating material. In the operation of the aspirator head of the invention suction is varied by the number of holes uncovered in the tube foraminous portion by reciprocation of the barrel on the valve tube, and as the liquids and solids are aspirated through the wand the holes can trap solids larger than themselves.

In the preferred form of the suction head of the invention the valve tube includes a cylindrical base rearwardly of the valve tube shaft and releasably secureable in the end fitting, and the barrel is sized to permit longitudinal passage rearwardly therethrough of the valve tube during assembly so that the valve tube base can extend rearwardly of the barrel annulus for insertion into and securement within the end fitting. It is also preferred that the cap comprises stop means preventing the barrel end annulus from displacement forwardly off the tube foraminous portion.

Latch means may be provided for releasably securing the valve tube base in the end fitting. O-ring means may also be provided for releasably holding the barrel end annulus at various pre-determined positions on the tube shaft and foraminous portions, including the position where all the holes are covered by the barrel end annulus and suction is stopped.

The holes in the tube foraminous portio may be formed in at least two circumferential rows allowing a corresponding number of suction settings depending on how many rows of holes are covered by the barrel end annulus.

The advantages of the variable suction aspirator head of the invention are self-evident in that it consists of only two parts which may be separated from the end fitting of the suction hose and from one another after each successive use and fully cleaned and sterilized even by brushing and heat sterilization, which is inappropriate for complicated prior art aspirator heads. In addition much of the solid debris removed from the mouth of the patient is trapped in the head itself and is disposed of after each successive use to avoid accumulation in a downstream trap.

DESCRIPTION OF PREFERRED EMBODIMENT

Figure 1:
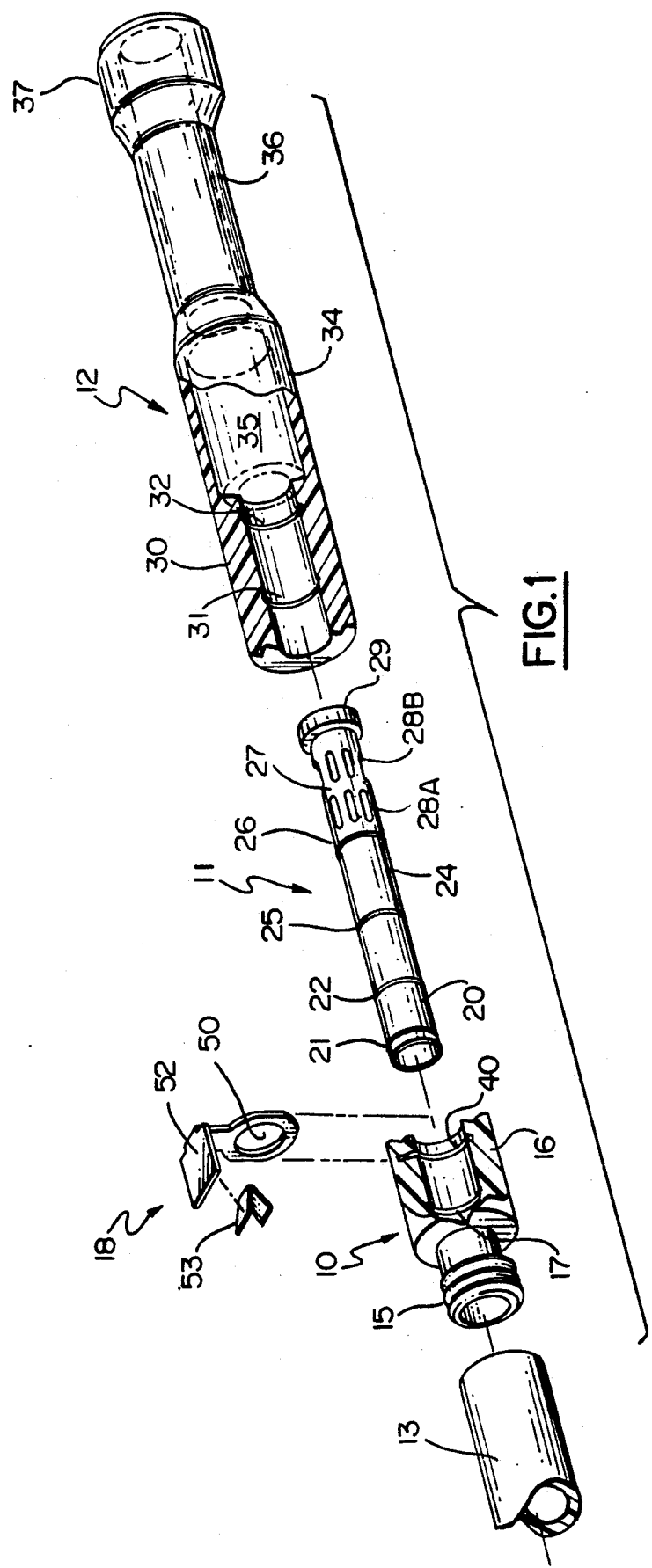
FIG. 1 is an exploded perspective view of the aspirator head of the invention showing the parts in their relative positions after assembly.
Figure 11:
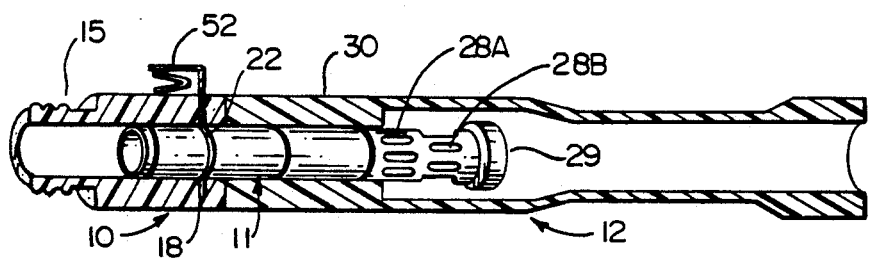
FIG. 11 shows the valve tube inserted in the end fitting with the head ready for operation at full suction.

Referring to FIG. 1 showing the parts of the apparatus in an exploded view but also in their relative positions after assembly, and also to FIG. 11 which shows the device as assembled and at the commencement of operation, it will be seen that the variable suction aspirator head of the invention is mounted on an end fitting 10 and consists simply of two parts, namely a valve tube 11 and a barrel 12. Each of these two parts is of generally circular cross section throughout its length and none has any moving parts of its own. What is referred to herein as the rearward end of the head is that at the left in FIG. 1 at the end fitting 10 where connection is made with a suction hose 13, and what is referred to herein as the forward end is that end of the barrel 12 at the right in FIG. 1.

The end fitting 10 includes an insert portion 15 with an appropriately ribbed surface for securement within the end of the suction hose 13. The end fitting 10 also includes a receiver portion 16 forwardly of the insert portion 15 and of greater inside diameter than the bore in the receiver portion 16. A circular groove 17 is formed within the bore of the receiver portion 16 of the end fitting 10. A releasable latch mechanism 18, described hereafter in relation to FIGS. 2 to 7, is also included in the end fitting 10.

Included in the valve tube 11 is a cylindrical base 20 about which a resilient O-ring 21 is positioned. The outside diameter of the cylindrical base 20 of the valve tube 11 is such that it fits snugly but slidably within the bore of the receiver portion 16 of the end fitting 10, and O-ring 21 is positioned to snap releasably into the groove 17. The cylindrical base 20 also includes an outer circular groove 22.

Also included in the valve tube 11 is a circumferentially complete shaft 24 forwardly of the cylindrical base 20. Two resilient O-rings 25 and 26 are spaced longitudinally apart about the shaft 24 of the valve tube 11. Forwardly of and of the same outside diameter as the shaft 24 is a foraminous portion 27 of the valve tube 11 formed with two longitudinally spaced circumferential rows of wall holes 28A and 28B. The valve tube 11 has an interior bore of the same inside diameter as the bore of the insert portion 15 of the end fitting 10. A disc-like cap 29 is affixed to and closes off the forward end of the foraminous portion 27 of the valve tube 11 and its diameter is slightly greater than the outside diameter of the valve tube 11.

The barrel 12 comprises an end annulus 30 with an inside diameter sized to sealably and slidably encircle the tube shaft 24 of the valve tube 11. Formed within the bore of the end annulus 30 are a pair of circular grooves 31 and 32 which are spaced apart the same as the O-rings 25 and 26. The bore of the end annulus 30 is smaller than the diameter of the cap 29 so that forward movement of the barrel 12 off the valve tube 11 is not possible. An enlarged portion 34 forwardly of the end annulus 30 defines an encircling chamber 35 around the tube foraminous portion 27. A tubular wand 36 is located forwardly of the enlarged portion 34 of the barrel 12 and is formed at its forward end with an enlarged socket portion 37 adapted to receive one of the several forms of conventional vacuum tips which may be selected for aspiration of saliva and dental debris in the course of dental work. During use the selected tip may be turned in any direction by rotating the barrel 12 on the valve tube 11. The bore of the barrel from the forward end of the socket portion 37 to the forward end of the end annulus 30 is great enough to allow passage of the cap 29 of the valve tube 11.

It is to be understood that the end fitting 10 remains on the end of the hose 13 and is not normally removed during use. However, as noted previously, the cylindrical base 20 of the valve tube 11 is intended to be releasably secured within the receiver portion 16 of the end fitting 10 and should be positively locked in place in its secured position. To accomplish this the latch mechanism 18 is provided and its structure and mode of operation are shown in FIGS. 2 through 7.

Figure 2:
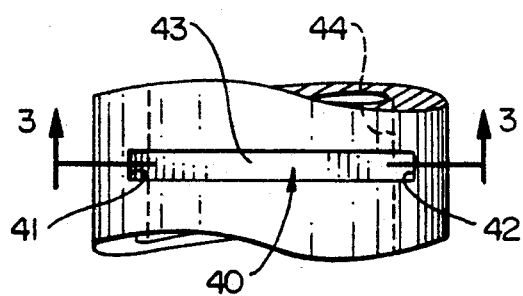
FIG. 2 is a fragmentary plan view of the end fitting showing a slot for receiving the latch means.
Figure 3:
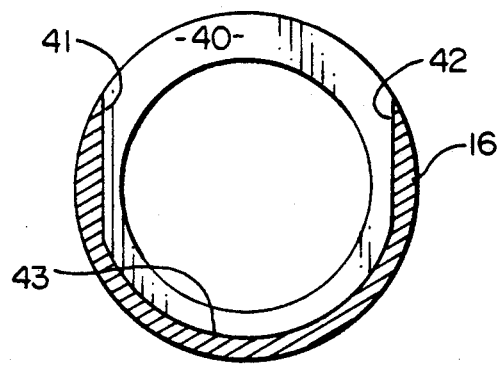
FIG. 3 is a section taken along the line 3—3 of FIG. 2.
Figure 4:
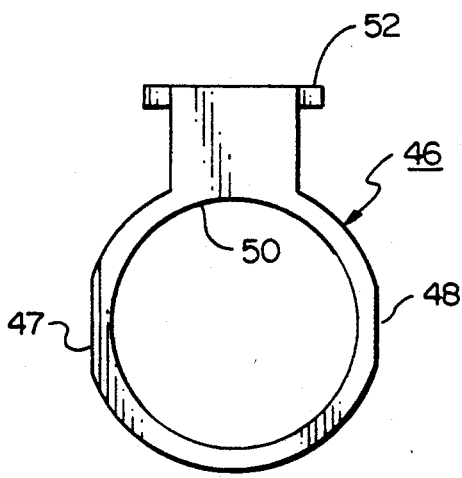
FIG. 4 is an elevation of a latch clip insertable in the slot of FIG. 3.
Figure 5:
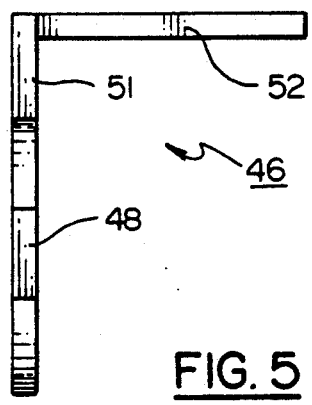
FIG. 5 is a side elevation of the clip of FIG. 4.
Figure 6:
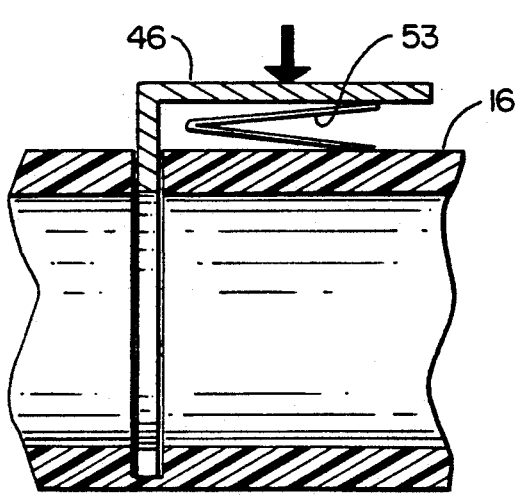
FIG. 6 is a fragmentary longitudinal section showing the clip assembled in the slot of the end fitting and biased into locking position.
Figure 7:
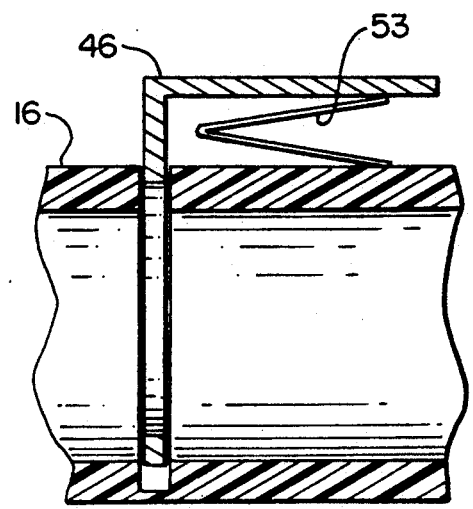
FIG. 7 is a view similar to FIG. 6 showing the clip displaced into release position.

Referring first to FIGS. 2 and 3 a lateral slot 40 is provided in the receiver portion 16 of the end fitting 10 and it has straight parallel side walls 41 and 42 and a curved bottom wall 43. These slot walls extend into the inside bore 44 of the receiver portion 16 of the end fitting 10. FIGS. 4 and 5 show a latch clip 46 which is sized to fit slidably down into the slot 40. It has straight parallel side edges 47 and 48 which slidably engage the side walls 41 and 42 of the slot 40. The clip 46 defines a circular inner periphery 50 which is equal in diameter to the diameter of the bore 44 of the receiver portion of the end fitting 10. A projection 51 at the top of the clip 46 has a finger button 52 extending laterally therefrom. As shown in FIGS. 6 and 7 a double acting leaf spring 53 is located between the underside of the button portion 52 and the outer surface of the receiver portion 16 of the end fitting 10. The spring 53 biases the clip 46 into a locking position as shown in FIG. 6 wherein the circular inner periphery 50 of the clip 46 is eccentric to the bore 44 of the receiver portion of the end fitting 10 and therefore projects upwardly into the inside of the end fitting 10 beyond the surface of the bore 44. In this position it is received within the groove 22 on the outside of the cylindrical portion 20 of the valve tube 11 thereby holding the valve tube 11 longitudinally in position on the end fitting 10 but allowing full relative rotation therebetween. When the valve tube 11 is to be either assembled to or disassembled from the end fitting 10 the button 52 is depressed downwardly in the direction of the arrow as shown in FIG. 7 against the force of the spring 53 until the inner circular periphery 50 of the clip 46 is concentric with the bore 44 of the receiver portion 16 of the end fitting 10, thereby releasing the clip 46 from the groove 55.

Figure 8:
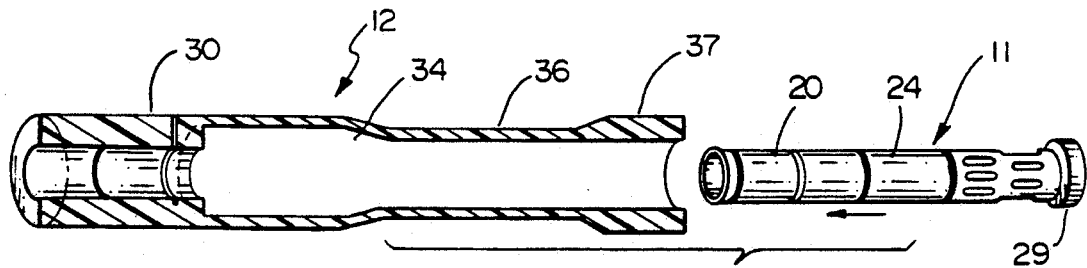
FIG. 8 is a perspective view partly in section of the head with the valve tube about to be inserted into the barrel in the first step of assembly.
Figure 9:
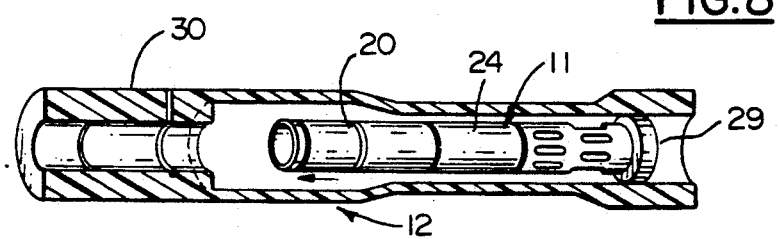
FIG. 9 is a similar view showing the valve tube passing through the barrel during assembly.
Figure 10:
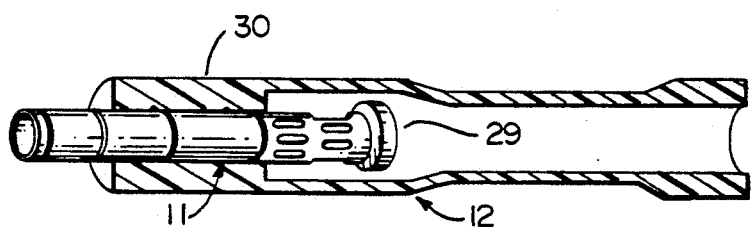
FIG. 10 shows the valve tube in its fully inserted position in the barrel during assembly.

FIGS. 8 through 13 illustrate the steps involved in assembling the aspirator head of the invention. Referring first to FIG. 8, the initial steps is to insert the valve tube 11 into the open forward end of the tubular wand 36. FIG. 9 shows the valve tube 11 continuing during its insertion with the cap 29 passing through the bore of the wand 36. Finally the shaft 24 of the valve tube 11 enters the end annulus 30 of the barrel 12 as shown in FIG. 10 and the O-rings 25 and 26 around the valve tube shaft 12 snap releasably into the grooves 31 and 32 in the end annulus 30. At this point the cylindrical base 20 of the valve tube 11 projects from the rearward end of the barrel 12.

The button 52 on the end fitting 10 is then actuated so that the latch mechanism 18 is activated from the position shown in FIG. 6 to the position shown in FIG. 7. The cylindrical base 20 of the valve tube 11 is then advanced into the end fitting 10 until the O-ring 21 snaps into the groove 17 and the circular periphery 50 of the clip 46 enters the groove 22 on the cylindrical base 20 of the valve tube 11. The valve tube 11 is then positively attached to the end fitting 10 and the assembly operation is complete.

In operation an appropriate vacuum tip (not shown) is inserted in the socket portion 37 of the wand 36 and suction is activated. This draws air into the forward end of the wand 36, through the enlarged portion 34 and chamber 35 of the barrel 12, through the wall holes 28A and 28B and then through the valve tube 11 into the end fitting 10. In use saliva and dental debris are drawn by this suction through the wand 36 and enlarged portion 34 of the barrel 12 but all solids larger than the wall holes 28A and 28B are trapped by the holes in the chamber 35 of the barrel 12. Liquids such as saliva and small solids can continue, however, and be aspirated into the downstream waste system of the dental facility.

Figure 12:
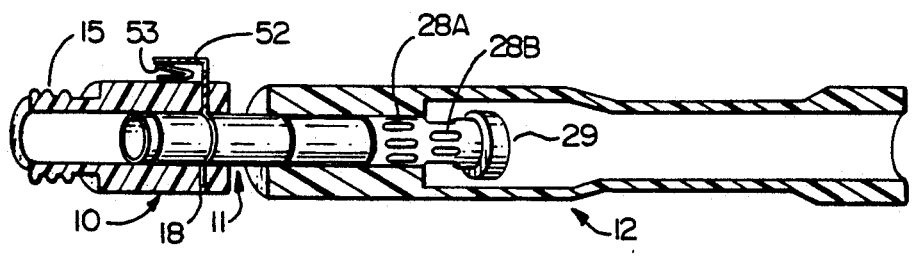
FIG. 12 shows the head during operation with the barrel advanced on the valve tube to the position of half suction.

The maximum amount of applied suction is achieved by setting the barrel end annulus 30 on the valve tube shaft 24 as shown in FIG. 11 with both circumferential rows of the holes 28A and 28B. If during operation it is desired to operate with less suction, as with a child patient or when only one operatory is being used, the barrel 12 is advanced forwardly from the position shown in FIG. 11 to that shown in FIG. 12 by releasably engaging the O-rings 25 and 26 from the grooves 31 and 32 so that the forward O-ring 26 is snapped releasably into the rearward groove 31 as shown in FIG. 12. In this position the forward row of wall holes 28B is still exposed but the rearward row 28A is covered by the end annulus 30 and suction is reduced accordingly.

Figure 13:
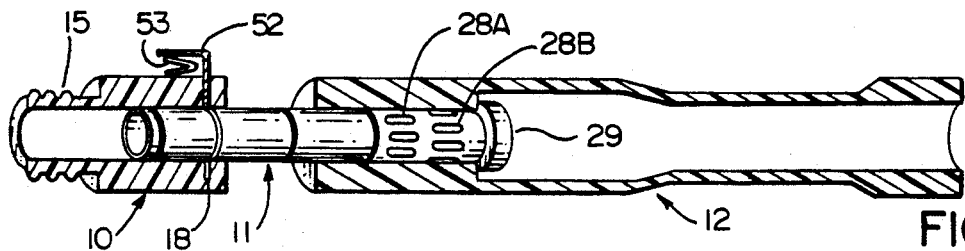
FIG. 13 illustrates the head during operation with the barrel advanced on the valve tube to zero suction.

If it is desired to stop suction altogether the barrel 12 is simply displaced forwardly still further from the position shown in FIG. 12 to that shown in FIG. 13 where the rearward lip of the cap 29 abuts the forward end of the annulus 30 and both rows of wall holes 28A and 28B are covered.

The aspirating head of the invention is easily disassembled. The button 52 of the latch mechanism 18 is depressed to its release position of FIG. 7 and the cylindrical base 20 of the valve tube 11 is simply pulled out of the receiver 16 of the end fitting 10 so that the barrel 12 and valve tube 11 appear as in FIG. 10. With any simple rod-like tool the valve tube 11 is then pushed forwardly through the barrel 12 from the position shown in FIG. 10 past the position shown in FIG. 9 until it is ejected from the forward end of the barrel 12 in the position shown in FIG. 8.

When the aspirator head of the invention is disassembled as described above, preferably after use on each successive patient, the solid material collected in the chamber 35 of the barrel 12 may be immediately removed, thus avoiding deposit of such solid material in the trap of the dental facility waste system where it might remain for hours and possibly contaminate downstream sewage systems. The barrel 12 and valve tube 11 can be thoroughly cleaned and sterilized after use on each patient. Since no moving parts or fragile structures are involved, this cleaning can include mechanical brushing, rinsing and heat sterilization.

The scope of the invention is to be determined by the following claims rather than by the foregoing description of preferred embodiment.

I claim:

1. A variable suction aspirator head with a solids trap for aspiration of material as from the mouth of a dental patient, the head having a rearward suction source end attached to an end fitting of a suction hose and a forward aspirating end, comprising
   a) a valve tube extending forwardly from the end fitting and comprising
      i. a shaft adjacent the end fitting,
      ii. a foraminous portion forwardly of and of the same outside diameter as the shaft and formed with longitudinally spaced wall holes, and
      iii. a cap closing off the forward end of the foraminous portion; and
   b) a barrel comprising
      i. an end annulus sized to sealingly and slidably encircle the tube shaft and adapted to be reciprocated along the foraminous portion to cover and uncover various of said holes,
      ii. an enlarged portion forwardly of the end annulus adapted to define a chamber around the tube foraminous portion, and
      iii. a tubular wand forwardly of the enlarged portion for aspirating material;
   c) whereby suction varied by the number of holes uncovered in the tube foraminous portion by reciprocation of the barrel on the valve tube can aspirate liquids and solids through the wand and the holes can trap solids larger than themselves.

2. A suction head according to claim 1 wherein the valve tube includes a cylindrical base rearwardly of the valve tube shaft and releasably securable in the end fitting, the barrel being sized to permit longitudinal passage rearwardly therethrough of the valve tube during assembly so that the valve tube base can extend rearwardly of the barrel end annulus for insertion into and securement within the end fitting.

3. A suction head according to claim 2 wherein said cap also comprises stop means at the forward end of the tube foraminous portion preventing the barrel end annulus from displacement forwardly off the tube foraminous portion.

4. A suction head according to claim 2 which includes latch means for releasably securing the valve tube base in the end fitting.

5. A suction head according to claim 1 wherein the holes in the tube foraminous portion are formed in at least two circumferential rows allowing a corresponding number of suction settings depending on how many rows of holes are covered by the barrel end annulus.

6. A suction head according to claim 1 which includes O-ring means for releasably holding the barrel end annulus at various pre-determined positions on the tube shaft and foraminous portions including a position wherein all the holes are covered by the barrel end annulus and suction is stopped.

7. A suction head according to claim 6 which includes latch means to releasably secure the valve tube base in the end fitting and O-ring means to releasably hold the barrel end annulus at its pre-determined position on the tube shaft.

8. A variable suction aspirator head with a solids trap for aspiration of material as from the mouth of a dental patient, the head having a rearward suction source end attached to an end fitting of a suction hose and a forward aspirating end, comprising
   a) a valve tube extending forwardly from the end fitting and comprising i. a cylindrical base releasably secured in the end fitting,
ii. a circumferentially complete shaft forwardly of the cylindrical base,
iii. a foraminous portion forwardly of and of the same diameter as the shaft and formed with at least two longitudinally spaced circumferential rows of wall holes, and
iv. a cap closing off the forward end of the foraminous portion and extending radially outwardly beyond its diameter to provide stop means; and b) a barrel comprising
i. an end annulus sized to sealingly and slidably encircle the tube shaft and adapted to be reciprocated along the foraminous portion to cover and uncover various rows of said holes,
ii. an enlarged portion forwardly of the end annulus adapted to define an encircling chamber around the tube foraminous portion, and
iii. a wand forwardly of the enlarged portion for aspirating material,
iv. the barrel being sized to permit longitudinal passage rearwardly therethrough of the valve tube during assembly until the cap stop means engages the end annulus so that the valve tube base can extend rearwardly of the end annulus for insertion and securement within the end fitting; and c) means for releasably holding the barrel end annulus at various pre-determined positions on the tube shaft and foraminous portions allowing a corresponding number of suction settings depending on how many rows of holes are covered by the barrel end annulus including a position wherein all the holes are covered by the barrel end annulus and suction is stopped;

d) whereby suction varied by the number of rows of holes uncovered in the tube foraminous portion by reciprocation of the barrel on the valve tube can aspirate liquids and solids through the wand and the holes can trap solids larger than themselves.

* * * * *